United States Patent [19]

Sheldon

[11] Patent Number: 4,573,963
[45] Date of Patent: Mar. 4, 1986

[54] OUTER TAMPON TUBE WITH FINGER GRIP

[75] Inventor: Donald A. Sheldon, Outagamie County, Wis.

[73] Assignee: Kimberly-Clark Corporation, Neenah, Wis.

[21] Appl. No.: 542,853

[22] Filed: Oct. 17, 1983

[51] Int. Cl.<sup>4</sup> ............................................. A61F 13/20
[52] U.S. Cl. ........................................ 604/15; 604/11
[58] Field of Search ..................................... 604/11–18

[56] References Cited

U.S. PATENT DOCUMENTS 3,429,312 2/1969 Stump .................................... 604/15
3,575,169 4/1971 Voss et al. ............................. 604/18

Primary Examiner—C. Fred Rosenbaum
Assistant Examiner—Sherri E. Vinyard
Attorney, Agent, or Firm—J. P. O'Shaughnessy; J. J. Duggan

[57] ABSTRACT

An outer tampon tube is provided with a finger gripping section on one end formed by a series of spaced circumferentially disposed slits, each slit being equidistant from the tube ends and indentations extending radially from the slits formed by crease lines extending from the bottom of the tube to the slits.

7 Claims, 2 Drawing Figures

OUTER TAMPON TUBE WITH FINGER GRIP

FIELD OF THE INVENTION

This invention relates to a tampon tube and particularly an outer tube with a finger grip at one end.

BACKGROUND OF THE INVENTION

Tampons have becomes a significant part of the feminine care market recently and the most popular type of tampons are the so-called tube tampons. These tampons have been inserted by a pair of mated telescoping tubes. The inner tube rests against the bottom of the tampon at one end and extends outward through the bottom of the outer tube. The top of the outer tube may be closed or partially shield the leading edge of the tampon, or, alternatively, may be open with the leading edge of the tampon exposed. The bottom of the outer tampon tube has some configurational features to aid in gripping such as a portion of reduced diameter (a necked-in portion) which provides a guide for the passage of the inner tube during the expulsion of the tampon and also a finger gripping area. When the tampon is expelled, the inner tube serves as a plunger pushing against the tampon through the leading or upper edge of the outer tampon tube traveling generally along the channel provided by the necked-in portion. U.S. Pat. No. 3,409,011 shows such an outer tube.

Other representative outer tube configurations can be found in U.S. Pat. No. 3,429,312 which shows an outer tube shaped having longitudinal undulations along the tube length. U.S. Pat. No. 3,696,812 shows an outer tube with a series of convex rings designed to enhance the finger grip pattern. As can be seen from the prior art cited above, conventional means of forming the finger grip area on the outer tube involve either the thickening of the area of the walls used in the finger grip portion or the addition of an extra shaped element or elements. When tampon tubes are made of plastic the difficulty in molding and the cost of the tube itself is substantially increased when elaborate geometric formations are chosen, or, when a tube having wall thickness greater than needed in the finger grip portion is constructed.

SUMMARY OF THE INVENTION

According to this invention an outer tampon tube is provided in which a finger grip area is formed by a series of circumferential slots positioned equidistantly from the bottom of the tampon tube with an indentation extending essentially from the center of the slots toward the bottom of the tube formed by a crease line. A simple easy to manufacture outer tampon tube is provided having a section of effectively reduced diameter to function as a guide for the inner tampon tube without increasing the wall thickness or the difficulty in manufacture.

The outer tube of this invention can be manufactured either from the thermoplastic material with the cutting and shaping performed on a mandril or from cardboard where the cutting, scoring, and creasing can be accomplished by traditional cardboard shaping means.

DETAILED DESCRIPTION OF THE INVENTION AND THE DRAWINGS

Figure 1:
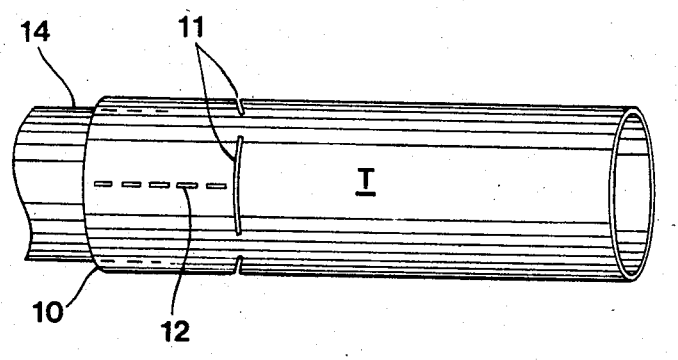
Figure 2:
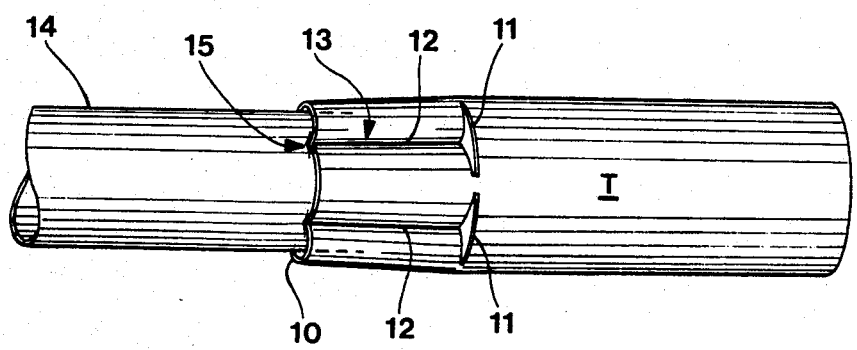

This invention may more readily be understood by reference to the drawings in which:

FIG. 1 is a side view of a tampon tube showing the fold or score line and cut slot in the tube blank; and FIG. 2 is an end view of the formed outer tube showing the spatial relationship of the components in conjunction with an inner tube.

As can be seen in FIG. 1 an outer tube T is formed with slots 11 positioned preferably between 0.5 and 4 centimeters from the bottom end of the tube (with 1.5 to 1.7 cm. preferred) and a score line shown by dotted line 12 extends from the approximate center of the slot to the outer end 10. Pressure is applied to this fold or score line 12 to form the indentations 13 extending along a path defined by the score lines. As can be seen by reference to FIG. 2 these creases form not only a detent on the outer surface of the outer tampon tube for finger retention but a series of ribs 15 on the inner surface of the outer tube in the finger grip portion corresponding to indentations 13. These ribs form a directional guide for travel of the inner tube 14 during the expulsion step.

The view shown in FIG. 2 depicts one-half of the tampon tube and, according to this invention, either one or two other sets of slits 11 and crease lines 12 will be positioned on the other half of the tube not shown. If there is only three slits, the slits may not be equal in length and may be positioned asymmetrically with respect to each other around the periphery of the tube. Either three slots with matching creases positioned equidistantly and of equal length or asymmetrically or four slots with matching creases positioned equidistantly can be utilized.

As can be seen from the drawings the crease lines and indentations extend from the slots to the bottom of the outer tube. These fold lines may also terminate before the bottom providing a second finger detent, although the outer tube with this second detent is more difficult generally to manufacture.

What is claimed is:

1. An outer tampon tube comprising:
an elongated tubular element having a longitudinal axis and two ends with an insertion portion at one end and a gripping portion at the other end,
said gripping portion having at least one longitudinally extending inwardly turned rib formed therein, said rib being formed by a slit extending through and around a portion of the circumference of said tubular element, and a longitudinally extending crease line associated with said slit, said crease line extending from said slit and toward an end, said crease line when indented radially inwardly on said tubular element forming said rib.

2. The outer tampon tube according to claim 1 wherein said crease extends from said slit to said other end.

3. The outer tampon tube according to claim 1 or 2 wherein there are three slits of about equal length equiangularly spaced around its circumference.

4. The outer tampon tube according to claim 1 or 2 wherein there are four slits of about equal length equiangularly spaced around its circumference.

5. The outer tampon tube according to claim 1 or 2 wherein each said slit is positioned between about 1.5 to 4 cm. from said other end.

6. An outer tampon tube comprising:
an elongated tubular element having a longitudinal axis and two ends, with an insertion portion at one end and a gripping portion at the other end,
said gripping portion having a plurality of spaced longitudinally extending inwardly turned ribs formed therein for engaging the outer surface of a tampon plunger element insertable within said gripping portion, said ribs being formed by a plurality of spaced slits extending generally around a circumference of said tubular element in the same general plane, and a plurality of longitudinal crease lines, a crease line extending from a respective slit and toward an end, said crease lines when indented radially inwardly on said tubular element forming said ribs.

7. The outer tampon tube of claim 6 wherein said crease lines extend from said slits to the gripping portion end of said tubular element.

* * * * *